United States Patent [19]

Novak et al.

[11] Patent Number: 5,554,113
[45] Date of Patent: Sep. 10, 1996

[54] FLOW PRESSURE TRANSDUCER

[75] Inventors: Pavel Novak, Schaffhausen; Clemens Rebholz, Uhldingen/Müllheim; Joachim Willner, Neunkirch, all of Germany

[73] Assignee: Storz Endoskop GmbH, Schaffhausen, Germany

[21] Appl. No.: 255,881

[22] Filed: Jun. 7, 1994

Related U.S. Application Data

[63] Continuation of Ser. No. 77,721, Jun. 17, 1993, abandoned.

[30] Foreign Application Priority Data

Jun. 17, 1992 [DE] Germany .......................... 42 19 888.7

[51] Int. Cl.$^6$ ................................................. A61M 1/00
[52] U.S. Cl. .............................................................. 604/30
[58] Field of Search ........................... 73/262, 269, 271, 73/715; 137/557; 604/31, 33, 65, 67, 247, 30

[56] References Cited

U.S. PATENT DOCUMENTS

| | | | |
|---|---|---|---|
| 4,398,542 | 8/1983 | Cunningham et al. | 73/715 |
| 4,444,198 | 4/1984 | Petra | 604/30 |
| 4,940,457 | 7/1990 | Olson | 604/247 |
| 5,152,746 | 10/1992 | Atkinson et al. | 604/67 |

*Primary Examiner*—Manuel Mendez
*Attorney, Agent, or Firm*—Antonelli, Terry, Stout & Kraus

[57] ABSTRACT

A medical pressure transducer is disclosed with a sterilizable pressure dome exhibiting two connections by means of which the pressure dome can be connected to a tube conduit system or the like, the internal pressure of which is to be measured, in such a way that the medium flowing through the tube conduit system passes through the inner space of the pressure dome.

The inner space of the pressure dome is constituted by a housing, a sterilizable pressure dome diaphragm transmitting the pressure to an unsterilized pressure sensor, and a relief valve.

6 Claims, 1 Drawing Sheet

FLOW PRESSURE TRANSDUCER

This application is a continuation of application Ser. No. 08/077,721, filed Jun. 17, 1993 and now abandoned.

BACKGROUND OF THE INVENTION

The invention relates to a pressure transducer for use in medical technology.

Tube pumps are utilized with great frequency for the transport of fluids for irrigation of body cavities, e.g. in endoscopic treatment processes. The tube system required for operation in such pumps, which system must be sterile, is designed either to be sterilizable and reusable or as a disposable tube set.

Such a tube kit comprises:

(a) a connection to a storage container (frequently a bag), (b) a pump segment of a silicone hose which is inserted in a tube pump, (c) a connection to a pressure sensor, (d) a relief valve providing passive safety, (e) a connection to a trocar or endoscope.

For separating the sterile interior of the tube set from the unsterilized pressure sensor it is known to use a "Millipore" filter wherein pressure measurement takes place indirectly by way of an air column. This solution has the following drawbacks in practical usage:

If the tube leg provided for the pressure measurement is not attached in time, or is attached incorrectly to the pressure pickup connection, then, on the one hand, a pressure measurement is impossible; on the other hand, liquid can rise in this tube leg and wet the air filter, thereby falsifying the pressure measurement, in certain cases even without being noticed, because then a pressure measurement via the air column is no longer possible. Furthermore, there is then also the possibility of liquid escaping from the pressure pickup connection.

Moreover, the use of a so-called pressure dome has likewise been known from the prior art:

In this case, a pressure dome containing a flexible diaphragm is connected to the tubing. This flexible diaphragm seals off the tubing. The pressure dome is connected to an unsterilized pressure sensor, for example, by means of a bayonet catch.

The pressure dome normally has two connections and a chamber sealed off by a diaphragm. The diaphragm is tensioned by way of a pressure pickup, thus permitting the pressure measurement within the sterile interior. The diaphragm must be of such a design that, if at all possible, it does not falsify the measurement, i.e. it must be sufficiently resilient with respect to the stiffness of the pressure pickup diaphragm. One connection serves for joining to the monitored tube system (for example infusion hose kit, catheter); the other one is utilized for venting purposes during the initial filling of the entire system.

The conventional pressure domes thus are located at the end of a side branch of the tube kit and permit pressure measurement within this tube kit (blood, infusion solution) while avoiding a coupling air cushion and/or the use of a sterile pressure pickup.

As for the state of the art, attention is invited, as a supplement, to the published patent disclosures DE 29 30 869 C3, DE 35 10 043 C2, and EP 0 208 955 A1; express reference is had to these disclosures, by the way, for an explanation of all terms not elaborated on in detail herein.

Furthermore, the relief valve is designed as a sterilizable, reusable part and, in the conventional systems, must be additionally incorporated into the tube system, for example by cutting the tubes open. This means that in case of user negligence the valve is not connected. Under excess pressure, the liquid will pass to the outside.

SUMMARY OF THE INVENTION

The invention is based on the object of indicating a pressure transducer universally usable in the medical field which, on the one hand, can be manipulated in a simplified fashion and, in particular, yields accurate results without venting and which, on the other hand, simplifies handling of the relief valve.

According to the invention, a medical pressure transducer with a sterilizable pressure dome has been provided, comprising two connections by means of which the pressure dome can be connected to a tube conduit system or the like, the internal pressure of which is to be measured, in such a way that the medium flowing through the tube conduit system flows through the interior of the pressure dome. This arrangement offers the substantial advantage that venting of the otherwise necessary and/or customary side branch does not become necessary, and handling is thus markedly facilitated.

In this connection, it is advantageous for the cross sections of the connections to be widened from the otherwise customary diameter of about 2 mm to about 5 mm so that it is possible to directly integrate the flow pressure dome into the respective tube kit, and to convey the irrigation fluid through this dome without an appreciable pressure loss.

Furthermore, according to the invention, the inner space of the pressure dome is bounded by a housing, a sterilizable pressure dome diaphragm transmitting the pressure to a pressure sensor, which latter is not sterilized, and a pressure relief valve.

Such a relief valve can be realized, for example, by providing the internal chamber of the pressure dome, with the two connections and the pressure-transmitting diaphragm, with a third opening sealed, for example, with a plastic disk by means of a correspondingly pretensioned compression spring.

This arrangement serves as a safety relief valve. Drainage of this relief valve takes place by way of the third connection.

Also this feature markedly facilitates handling because the relief valve need not be separately integrated into the tube kit and sterilized. Additionally, functional safety is enhanced because the safety valve is automatically always in the tube kit and cannot be forgotten.

The drainage means for this safety valve can, in principle, be left open as done heretofore and/or it can lead into a container.

However, advantageously, this drainage means is connected to the inlet of the rotary pump. Accordingly, in case of failure (breakdown of electronic pressure monitoring) the irrigation fluid is merely recirculated within a short tube section. However, in this arrangement, it is to be noted that the relative level difference between the pump (pressure dome with integrated relief valve) and the storage container normally suspended at a stand will affect the response pressure of the relief valve in correspondence with the water column lying therebetween.

Consequently, the response pressure can also be increased or, respectively, lowered intentionally by the users.

BRIEF DESCRIPTION OF THE DRAWINGS

The invention will be described hereinbelow by way of example with the use of an embodiment with reference to the drawings wherein.

DESCRIPTION OF THE PREFERRED EMBODIMENT

Figure 1A:
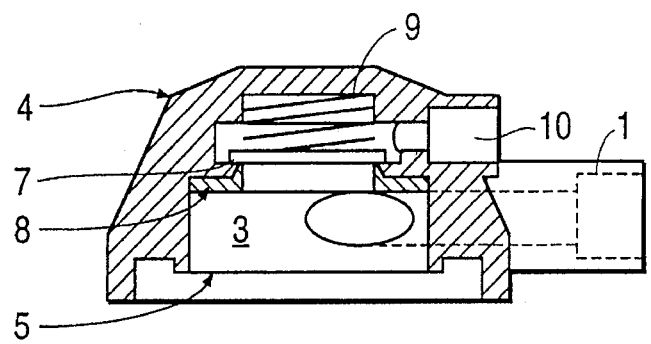
FIGS. 1a and 1b show a cross section and a top view of a pressure transducer according to this invention.
Figure 1B:
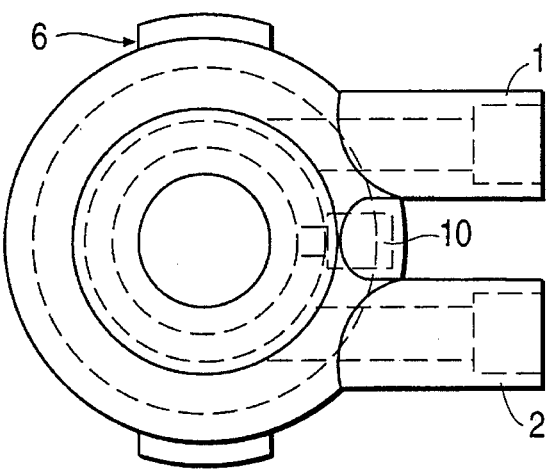

FIGS. 1a and 1b show, in a cross-sectional view and in a top view, a part of a medical pressure transducer, namely the sterilizable pressure dome. The pressure dome exhibits two connections 1 and 2 by means of which the pressure dome can be connected to a tube conduit system or the like, shown in greater detail in FIG. 2, the internal pressure of which is to be mesured, in such a way that the medium flowing through the tube conduit system passes through the inner space 3 of the pressure dome. For this purpose, the two connections 1 and 2 have cross-sectional dimensions of at least 4 mm, typically 5 mm.

The inner space 3 is formed, on the one hand, by the housing 4 of the pressure dome and, on the other hand, by a sterilizable pressure dome diaphragm 5 transmitting the pressure to an unsterilized pressure sensor (not shown) and by a relief valve which will be described in greater detail below.

A bayonet catch 6 is provided for connecting the illustrated part of the pressure transducer with the pressure sensor proper.

The relief valve is constituted by a plastic valve plate 7 which, in the basic condition, is in contact with a valve seat 8 and by a compression spring 9 pretensioning the valve plate 7. On the outlet side, the relief valve is connected to a drainage means Furthermore, exemplary dimensions are indicated in FIG. 1 in millimeters.

Figure 2:
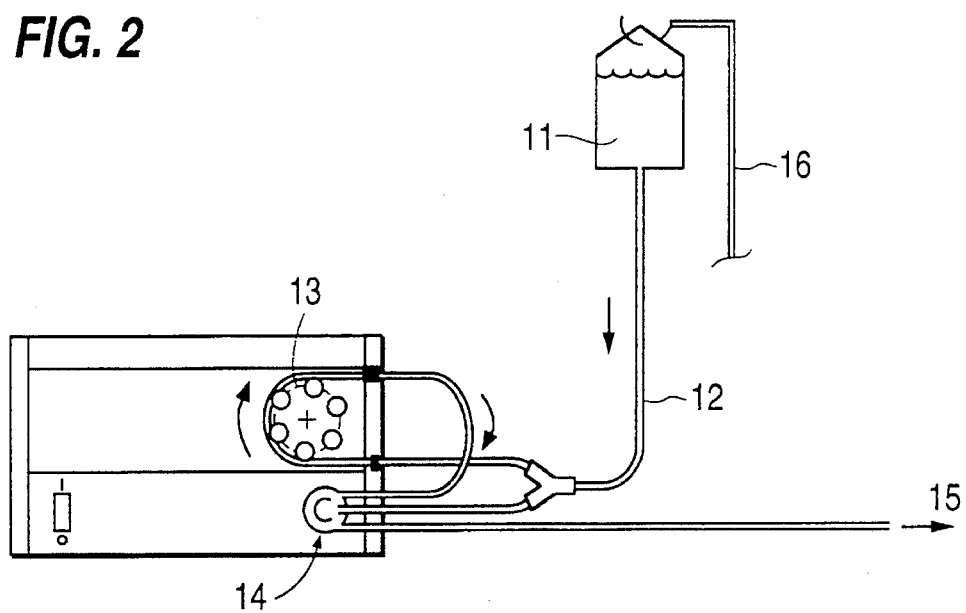
FIG. 2 shows the integration of the pressure transducer illustrated in FIG. 1 into an insufflation system.

FIG. 2 shows the integration of the pressure transducer shown in FIG. 1 into a insufflation system comprising a storage bag 11 for the fluid to be insufflated, a tube conduit system 12, a rotary or tube pump 13, and the pressure transducer 14 illustrated in FIG. 1. Numeral 15 denotes the feed end to the patient.

The drain 10 of the pressure dome is connected to the inlet of the rotary pump 13.

The response pressure of the relief valve can be adjusted by setting the level difference between the pressure dome 14 with integrated relief valve and the storage container 11 for the medium, this container being attached to a stand 16.

We claim:

1. A medical pressure transducer comprising a sterilizable pressure dome having two connection means for attaching fluid inflow and outflow tubes to said pressure dome, an inner housing within said pressure dome in fluid communication with said two connection means having a sterilizable pressure dome diaphragm for sensing the pressure within said housing and transmitting said pressure to an unsterilized pressure sensor connected to said pressure dome, and a relief valve within said housing connected to a drain for allowing excess fluid to escape said housing when said relief valve experiences pressures above normal.

2. The pressure transducer according to claim 1, wherein said inflow and outflow tubes exhibit cross-sectional dimensions of at least 4 min.

3. The pressure transducer according to claim 1 or 2, wherein said relief valve comprises a spring loaded valve plate which, in its normal condition, is in contact with a valve seat that forms a wall within said housing.

4. The pressure transducer of claim 3, wherein the valve plate comprises a plastic disk pretensioned by a compression spring.

5. The pressure transducer of claim 4, wherein the drain is connected to the inlet of a rotary or tube pump.

6. The pressure transducer according to claim 3, wherein a response pressure can be adjusted by setting a pressure level difference between the housing pressure within the dome and the pressure at the source of the fluid.

* * * * *